US012192357B2

(12) United States Patent
Reiman et al.

(10) Patent No.: US 12,192,357 B2
(45) Date of Patent: Jan. 7, 2025

(54) DEVICE AND LOCATION AUTHENTICATION FOR SECURE PATIENT MONITORING

(71) Applicant: Anelto, Inc., The Colony, TX (US)

(72) Inventors: Michael James Reiman, Plano, TX (US); Roy William Henke, Allen, TX (US); Scott D. Constien, Plano, TX (US)

(73) Assignee: Anelto, Inc., The Colony, TX (US)

( * ) Notice: Subject to any disclaimer, the term of this patent is extended or adjusted under 35 U.S.C. 154(b) by 318 days.

(21) Appl. No.: 17/740,776

(22) Filed: May 10, 2022

(65) Prior Publication Data

US 2022/0360444 A1 Nov. 10, 2022

Related U.S. Application Data

(60) Provisional application No. 63/186,495, filed on May 10, 2021.

(51) Int. Cl.
*H04L 9/32* (2006.01)
*G16H 80/00* (2018.01)
*H04W 12/037* (2021.01)

(52) U.S. Cl.
CPC ............. *H04L 9/321* (2013.01); *G16H 80/00* (2018.01); *H04W 12/037* (2021.01)

(58) Field of Classification Search
CPC ...... H04L 9/321; G16H 80/00; H04W 12/037
See application file for complete search history.

(56) References Cited

U.S. PATENT DOCUMENTS

| | | | | |
|---|---|---|---|---|
| 9,832,649 | B1* | 11/2017 | Curran | .................. H04W 12/02 |
| 11,615,257 | B2* | 3/2023 | Chronos | .............. A61B 5/4842 |
| | | | | 340/10.3 |
| 11,769,577 | B1* | 9/2023 | Dods | ...................... G16H 20/10 |
| | | | | 705/50 |
| 2010/0228977 | A1* | 9/2010 | Sievert | ............... A61N 1/37282 |
| | | | | 713/168 |
| 2013/0268444 | A1* | 10/2013 | Namgoong | ............. H04L 63/08 |
| | | | | 726/4 |
| 2014/0229339 | A1* | 8/2014 | Massiere | ................ G06Q 20/40 |
| | | | | 705/26.81 |
| 2015/0286791 | A1* | 10/2015 | Altobello | ............... G16H 40/67 |
| | | | | 705/3 |
| 2016/0095146 | A1* | 3/2016 | Ren | ........................ H04W 48/20 |
| | | | | 370/329 |
| 2019/0082968 | A1* | 3/2019 | Karnik | ...................... A61B 5/01 |
| 2020/0387887 | A1* | 12/2020 | Rathod | .............. G06Q 20/3224 |
| 2021/0019541 | A1* | 1/2021 | Wang | .................... G06V 40/172 |
| 2021/0118579 | A1* | 4/2021 | Morris | .................... G16H 80/00 |
| 2021/0196406 | A1* | 7/2021 | Mahadik | ............. G06F 21/6218 |
| 2021/0407668 | A1* | 12/2021 | Fish | ....................... H04L 63/101 |
| 2022/0070666 | A1* | 3/2022 | Hua | ....................... H04L 9/0866 |

(Continued)

*Primary Examiner* — Stephen T Gundry
(74) *Attorney, Agent, or Firm* — Honigman LLP; Grant Griffith

(57) ABSTRACT

A local hub maintains a secure and isolated connection with a device management server for reporting clinical data received from connected medical devices. Only authorized medical devices can communicate with the local hub and a list of allowed medical devices is managed by using a clinical application. A wearable device may be utilized to ensure that the user is within an acceptable range of the local hub.

8 Claims, 1 Drawing Sheet

(56) References Cited

U.S. PATENT DOCUMENTS

| | | | | |
|---|---|---|---|---|
| 2023/0059887 A1* | 2/2023 | Ohno | .................. | H04L 63/0861 |
| 2023/0093580 A1* | 3/2023 | Gaudet | ............... | G06F 21/6245 |
| | | | | 726/4 |
| 2023/0116997 A1* | 4/2023 | Morris | ................... | G16H 10/60 |
| | | | | 715/771 |
| 2023/0171302 A1* | 6/2023 | Supramaniam | ......... | H04L 63/08 |
| | | | | 709/203 |
| 2023/0208626 A1* | 6/2023 | Nix | ...................... | H04L 9/3247 |
| | | | | 713/171 |
| 2023/0215530 A1* | 7/2023 | McNair | ................. | G16H 10/65 |
| | | | | 235/375 |
| 2023/0231931 A1* | 7/2023 | Wittner | .................. | H04L 67/12 |
| | | | | 709/203 |
| 2023/0254378 A1* | 8/2023 | Durrant | ................. | G16H 40/40 |
| | | | | 709/217 |
| 2023/0380701 A1* | 11/2023 | Ahmed | .................. | G16H 50/20 |
| 2024/0048591 A1* | 2/2024 | Weiler | ................ | H04L 63/0823 |

* cited by examiner

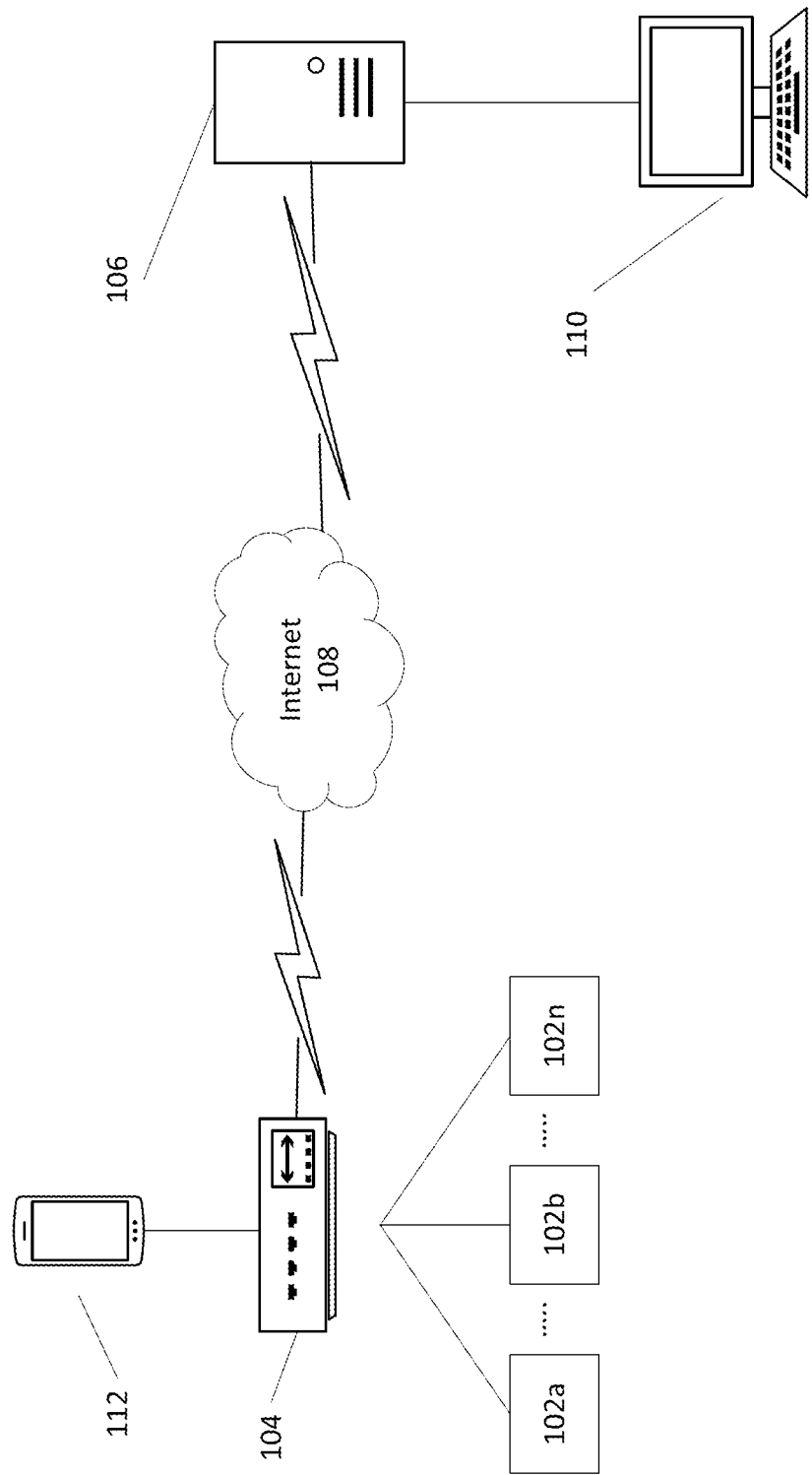

DEVICE AND LOCATION AUTHENTICATION FOR SECURE PATIENT MONITORING

CROSS-REFERENCE TO RELATED APPLICATIONS

This application claims priority to U.S. Provisional Patent Application Ser. No. 63/186,495, filed May 10, 2021, the entire contents of which are hereby incorporated by reference in their entirety.

BACKGROUND

Telehealth and Remote Patient Monitoring devices can potentially expose user's health data and are targets of hackers to gain access to patient data and network intrusion. This is especially problematic since many monitoring devices are now capable of wireless communications. Thus, a need exists for a system and method to secure and authenticate users and devices throughout the entire system.

SUMMARY

A local hub maintains a secure and isolated connection with a device management server for reporting clinical data received from connected medical devices. Only authorized medical devices can communicate with the local hub and a list of allowed medical devices is managed by using a clinical application. A wearable device may be utilized to ensure that the user is within an acceptable range of the local hub.

BRIEF DESCRIPTION OF THE DRAWINGS

FIG. 1 depicts a network diagram of the remote monitoring system of the present invention.

DETAILED DESCRIPTION

FIG. 1 depicts a network diagram of remote monitoring system 100 according to an embodiment of the present invention. A plurality of monitoring devices 102a . . . 102n are coupled to local hub 104. In a preferred embodiment, the monitoring devices 102a-102n are preferably wirelessly coupled to local hub 104 via a communication standard such as Bluetooth, Wi-Fi, or multiple simultaneous connections. However, local hub 104 is also capable of directly coupling to monitoring devices by wire if needed (e.g., USB) if support of legacy monitoring devices is required.

The monitoring devices 102a-102n may be any devices capable of measuring any number of vital signs of a user which may include, but are not limited to, blood pressure, weight, blood oxygen level, glucose levels, etc.

Local hub 104 is preferably a touch screen style device with/without a keyboard. This allows users to easily set up and connect monitoring devices 102a-102n. Further, as most users are now familiar with touch screen interfaces, even elderly or less computer literate people can use local hub 104 easily.

Local hub 104 may employ a custom operating system, only allowing it for use with remote monitoring system 100, or may be controlled via an application running on a smartphone or tablet. Preferably local hub 104 is capable of various types of wireless communication including cellular, Wi-Fi, and Bluetooth. Local hub 104 preferably may incorporate a GPS sensor so that the exact location of the local hub 104 can constantly be monitored.

Local hub 104 collects the data from the monitoring devices 102a-102n, formats the data, and transmits it to a device management server 106 over internet 108. The device management server 106 stores data for a plurality of patients, each of which has their own unique local hub 104. A clinician can view the stored data on device management server 106 using clinical application 110. The clinician can also use clinical application 110 to send messages to patients using local hub 104 (e.g., voice or text) and can also configure settings for the various monitoring devices 102a-102n if necessary. This allows the clinician to control the settings for the monitoring devices 102a-102n because users likely would not be familiar with the requirements of configuring monitoring devices 102a-102n past an initial setup.

As previously discussed, wireless networks and communication methods are subject to being compromised. Wireless scale 102a is preferably coupled to local hub 104 remotely using each device's unique identifier without a human in the loop. Local hub 104 is coupled to device management server 106 with 2-factor authentication over internet 108. Employing 2-factor (or more authentication for each connection) greatly reduces and/or eliminates the possibility of any information being hacked.

Described below are some examples of how 2-factor authentication can be implemented between the various components of remote monitoring system 100. First, it is important to ensure that only local hubs 104 are capable of communication with device management server 106 for the purpose of reporting patient information. In a preferred embodiment, each local hub 104 sends a service request including an identifier unique to local hub 104 to device management server 106 over internet 108. The device management server 106 responds with a communication via another communication channel, such as by using an SMS with a challenge payload sent over a cellular network. The local hub 104 captures the SMS, extracts the payload (preferably encrypted), and sends a return IP message over Internet 108 with the payload. The return IP message could also be sent using SMS, but utilizing different wireless communication channels helps to reduce the possibility of information being intercepted. Once the device management server 106 receives the returned message, it can authenticate the local hub 104 as a valid device that is retained in a database of approved devices stored on device management server 106 (e.g., using the identifier). The described process can also be carried out each time that local hub 104 communicates with device management server 106 or it can occur randomly or according to a set schedule.

Device management server 106 may also utilize other forms of authentication, such as requiring local hub 104 to self-report its GPS location (or cellular triangulation) or it can send any WiFi SSIDs it "sees" and the device management server 106 can determine the location. Communication between local hub 104 and device management server 106 is only allowed if local hub 104 is within a certain range of set GPS locations. For example, a first GPS location could be a user's home and a second GPS location may be a user's work, wherein the user moves the local hub 104 from location to location as needed. If the reported GPS location is not within a predetermined distance of each GPS location, communication is restricted. If the local hub 104 is reported as being outside the allowable GPS locations for too long, any further communication may be restricted until allowed by a clinician using clinical application 110 or a device management application. This may be an indication the local hub 104 has been lost or stolen and no further communication should be allowed. A remote wipe of local hub 104 may also be enabled by a clinician in these situations.

In another embodiment, if the reported or determined GPS location is outside the allowable range, other forms of authentication may be required such as requiring the user to enter a passkey on the local hub 104.

Preferably, most monitoring devices 102a-102n are coupled to local hub 104 via a Bluetooth connection. This requires devices to be paired and within a relatively short range of each other in order for communication to occur, which already provides a limited form of authentication. In some embodiments, each monitoring devices 102a-102n may be assigned a unique passkey which is not shown on a display of the monitoring device 102a-102n or contained on its packaging. For example, the passkey can be set for each device by a clinician using clinical application 110. In order to couple a monitoring device 102a-102n to local hub 104, the user would also need to enter the passkey assigned by the clinician. This helps to prevent monitoring devices 102a-102n with being paired with other local hubs 104, especially since the passkey can be changed.

In some embodiments, each user may be given a separate and unique wearable 112 that may include the functionality of an activity tracker or panic button. Each time a vital sign is reported to local hub 104 by any monitoring device 102a-102n, the local hub 104 searches for presence of the wearable 112. The authentication can be as simple as using the unique Bluetooth identifier that every device has to actually installing a crypto key inside the wearable 112. If the local hub 104 does not "see" the authorized wearable in proximity of the local hub 104, the reading is flagged as suspect. Any communication from the local hub 104 can also be locked or deactivated when the authorized wearable 112 is not in range of the local hub 104. This will prevent non-authorized users from accessing potentially sensitive medical information.

Periodically, local hub 104 preferably reports a list of all identifiers for monitoring devices 102a-102n that are in communication with local hub 104 to device management server 106 at regular intervals. Only approved devices and authorized Bluetooth medical devices are allowed to send data local hub 104. If remote management server 106 detects data received from a non-approved device, that data is flagged for further review by a clinician.

In some embodiments, device management server 106 provides a unique whitelist of approved identifiers and only monitoring devices 102a-102n with identifiers in the whitelist are allowed to communication with device management server 106. This is referred to as "pairing" and is managed using a clinical application 110 or device management server 106.

In some embodiments, two remote applications control or communicate with local hub 104. A first clinical application is utilized to control where vital sign data is sent and where the unique patient information is stored. A device management application that controls the configuration (pairing BLE vital measurement equipment), cellular and WiFi settings, handles all aspects of security such as authentication and location challenges. The device management application is will shut down or restrict use if a security breach is suspected.

Although various embodiments have been described with reference to a particular arrangement of parts, features, and the like, these are not intended to exhaust all possible arrangements or features, and indeed many other embodiments, modifications, and variations will be ascertainable to those of skill in the art. Thus, it is to be understood that the invention may therefore be practiced otherwise than as specifically described above.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A method of authenticating a plurality of medical devices for secure patient monitoring, the method comprising:
   coupling the plurality of medical devices to a local hub;
   sending, to the local hub, a first encrypted message via a first wireless communication method from a device management server, the first encrypted message comprising a payload;
   extracting the payload from the first encrypted message at the local hub;
   sending, from the local hub to the device management server, a second encrypted message containing the payload extracted from the first encrypted message by a second wireless communication method different than the first wireless communication method; and
   extracting the payload from the second encrypted message at the device management server;
   authenticating the local hub if the payload in the second encrypted message matches the payload in the first encrypted message.

2. The method of claim 1, further comprising:
   establishing a direct communication link between the local hub and the device management server; and
   preventing communication with the local hub over the Internet from any device other than the device management server.

3. The method of claim 1, further comprising:
   transmitting a whitelist of approved medical devices from the plurality of medical devices to the local hub; and
   preventing communication from any medical devices of the plurality of medical devices with the local hub for any medical devices not on the whitelist of approved medical devices.

4. The method of claim 1, further comprising:
   periodically sending a location of the local hub to the device management server; and
   disconnecting the local hub if the location is not within one or more predetermined areas.

5. The method of claim 1, wherein the first encrypted message comprises a short message service (SMS) message.

6. The method of claim 5, wherein the second encrypted message comprise an Internet protocol (IP) message.

7. The method of claim 1, wherein the local hub is authenticated by the device management server at random intervals.

8. The method of claim 1, wherein the local hub is wiped if the local hub is not authenticated by the device management server after a predetermined number of tries.

* * * * *